(12) United States Patent  (10) Patent No.: US 9,031,392 B2
Hsiao  (45) Date of Patent: May 12, 2015

(54) ANGLE-ADJUSTABLE AROMA DIFFUSER (71) Applicant: Serene House International Enterprise Ltd., Tortola (VG)

(72) Inventor: Ming Jen Hsiao, Miaoli County (TW)

(73) Assignee: Serene House International Enterprise Ltd., Tortola (VG)

( * ) Notice: Subject to any disclaimer, the term of this patent is extended or adjusted under 35 U.S.C. 154(b) by 99 days.

(21) Appl. No.: 13/870,829

(22) Filed: Apr. 25, 2013

(65) Prior Publication Data

US 2014/0126893 A1   May 8, 2014

Related U.S. Application Data (63) Continuation-in-part of application No. 13/669,402, filed on Nov. 5, 2012, and a continuation-in-part of application No. 13/669,411, filed on Nov. 5, 2012, now Pat. No. 8,787,739.

(51) Int. Cl.
A61H 33/06 (2006.01)
F24F 6/00 (2006.01)
A61L 9/03 (2006.01)

(52) U.S. Cl.
CPC ......................................... *A61L 9/03* (2013.01)

(58) Field of Classification Search
None
See application file for complete search history.

(56) References Cited

U.S. PATENT DOCUMENTS

| | | | | |
|---|---|---|---|---|
| 949,606 A * | 2/1910 | Tetherow | ....................... | 219/429 |
| 1,431,719 A * | 10/1922 | Brown | ......................... | 392/403 |
| 1,547,160 A * | 7/1925 | Bailey | ............................ | 219/473 |
| 2,043,647 A * | 6/1936 | Berven | .......................... | 261/136 |
| 2,742,342 A * | 4/1956 | Dew et al. | ........................ | 422/37 |
| 2,881,303 A * | 4/1959 | Resk | ............................. | 392/403 |
| 3,959,642 A * | 5/1976 | Turro | ............................... | 362/92 |
| 4,544,592 A * | 10/1985 | Spector | .......................... | 428/68 |
| 4,647,433 A * | 3/1987 | Spector | ......................... | 422/125 |
| 4,781,895 A * | 11/1988 | Spector | ......................... | 422/125 |
| 5,647,052 A * | 7/1997 | Patel et al. | ..................... | 392/390 |
| 5,651,942 A * | 7/1997 | Christensen | ................... | 422/125 |
| 5,796,914 A * | 8/1998 | Gatzemeyer et al. | ......... | 392/390 |
| 6,031,967 A * | 2/2000 | Flashinski et al. | ............ | 392/390 |
| 6,085,026 A * | 7/2000 | Hammons et al. | ............ | 392/390 |
| 6,349,168 B1 * | 2/2002 | Jaworski | ........................ | 392/392 |
| 6,663,838 B1 * | 12/2003 | Soller et al. | ................... | 422/125 |
| 6,772,756 B2 * | 8/2004 | Shayan | ..................... | 128/203.26 |
| 7,046,919 B2 * | 5/2006 | Shimizu et al. | ................ | 392/390 |
| 7,095,953 B2 * | 8/2006 | Caserta et al. | ................. | 392/390 |
| 7,572,412 B2 * | 8/2009 | Yang | .............................. | 422/124 |
| 7,670,566 B2 * | 3/2010 | Adair et al. | .................... | 422/125 |
| 8,047,837 B2 * | 11/2011 | Furner et al. | ................... | 431/291 |
| 8,066,420 B2 | 11/2011 | Hsiao | | |
| 8,147,116 B1 | 4/2012 | Hsiao | | |
| 8,262,277 B2 * | 9/2012 | Hsiao | ............................ | 362/643 |
| 8,265,466 B2 * | 9/2012 | Jorgensen | ...................... | 392/393 |
| 8,281,514 B2 * | 10/2012 | Fleming | .......................... | 43/129 |

(Continued)

*Primary Examiner* — Thor Campbell
(74) *Attorney, Agent, or Firm* — Ming Chow; Sinorica, LLC (57) ABSTRACT

An angle-adjustable aroma diffuser includes a housing defining opposing first opening and second opening, a aroma container mounted in the housing, a resistor attached to the bottom side of the aroma container, an aroma device put in the aroma container, and an electric plug pivotally coupled to the second opening of the housing and electrically connected with the resistor and connectable to an external power socket for conducting electricity to the resistor to produce heat so that the aroma container can transfer produced heat to the aroma device, causing the aroma device to give off a pleasant smell.

20 Claims, 8 Drawing Sheets

(56) References Cited

U.S. PATENT DOCUMENTS

| | | | |
|---|---|---|---|
| 8,716,632 B1* | 5/2014 | Pesu et al. | 219/438 |
| 8,750,694 B1* | 6/2014 | Porretta et al. | 392/395 |
| 2002/0176704 A1* | 11/2002 | Roe | 392/393 |
| 2005/0016985 A1* | 1/2005 | Haas et al. | 219/438 |
| 2005/0274818 A1* | 12/2005 | Ghazarian | 239/34 |
| 2007/0014549 A1* | 1/2007 | Demarest et al. | 392/393 |
| 2007/0047931 A1* | 3/2007 | Niemeyer | 392/390 |
| 2008/0013932 A1* | 1/2008 | He et al. | 392/390 |

\* cited by examiner

ANGLE-ADJUSTABLE AROMA DIFFUSER

CROSS-REFERENCE TO RELATED ART

The present invention is a continuation-in-part of and claims a priority to U.S. patent application Ser. No. 13/669,402 filed on Nov. 5, 2012 and application Ser. No. 13/669,411 filed on Nov. 5, 2012.

BACKGROUND OF THE INVENTION

1. Field of the Invention

The present invention relates to aroma diffusing technology and more particularly, to an angle-adjustable aroma diffuser, which allows change of the diffusing angle of the aroma diffuser.

2. Description of the Related Art

Many aroma diffusing devices are known and commercially available. Exemplars are seen in U.S. Pat. No. 8,066,420 entitled "Aroma diffusing night lamp system having an angle-adjustable electric plug (5)", U.S. Pat. No. 8,262,277A entitled "Aroma diffusing night lamp system with an angle-adjustable electric plug (5)", and U.S. Pat. No. 8,147,116 entitled "Safety lamp bulb connector assembly". These aroma diffusing devices commonly include a power source, a lamp, and a container for holding an essential oil or aromatic substance. Dumping of these aroma diffusing devices can be prone to danger. Further, after each use, the user needs to remove essential oil or aromatic substance residues from the container, and then to clean or wash the device, and then to put a new amount of essential oil or aromatic substance in the container, complicating the essential oil or aromatic substance supplying operation.

Further, most conventional aroma diffusing devices do not allow change of the diffusing direction or electric plug installation angle to fit different application requirements, different application places or different electric socket positions. Further, conventional aroma diffusing devices are commonly designed for use in particular places. For example, an aroma diffusing device designed for home or office use may be not suitable for use in a car. Further, the prior art aroma diffusing devices that allow change of the diffusing angle have the drawbacks of complicated structure, high manufacturing cost and high failure rate.

Therefore, it is desirable to provide an aroma diffuser that eliminates the aforesaid problems.

SUMMARY OF THE INVENTION

The present invention has been accomplished under the circumstances in view. It is main object of the present invention to provide an angle-adjustable aroma diffuser, which has the advantages of diffusing angle adjustability, simple structure, high durability, wide application range and high applicability.

To achieve this and other objects of the present invention, an angle-adjustable aroma diffuser in accordance with the present invention includes a housing, an aroma container, a resistor, and an electric plug. The housing defines opposing first opening and second opening. The aroma container is mounted in the housing, defining a top open side facing toward the first opening of the housing. The resistor is mounted at the bottom side of the aroma container. The electric plug is pivotally connected to the second opening of the housing and electrically coupled with the resistor. Thus, the housing and the electric plug can be biased relative to each other to adjust the angle defined therebetween. Further, the electric plug is electrically connected to a power source. By means of biasing the housing relative to the electric plug, the first opening of the housing and the top open side of the aroma container can be disposed facing upward. Further, an aroma device can be put in the aroma container. When the resistor is electrically conducted, it creates heat. The heat created by the resistor can be transferred to the aroma container to heat the aroma device, causing the aroma device to give off a pleasant smell. Further, the angular position of the housing can be adjusted relative to the electric plug, thereby reducing space occupation.

Further, the electric plug can be configured to fit any of a variety of electric sockets that are provided at any location and in any angle in a house, office, motor vehicle or aircraft. By means of biasing the housing relative to the electric plug, the top open side of the aroma container and the loaded aroma device can be kept facing upward, avoiding dumping.

Further, the angle-adjustable aroma diffuser can be used with a disposable aroma device. During application, the disposable aroma device is put in the aroma container for heating by the heat created by the resistor. The aroma device can be an aroma capsule containing therein an aromatic substance, an aroma stone filled up with an essential oil or fluid aromatic substance, or an absorber (sponge, nonwoven fabric, cotton cloth) absorbing an essential oil or fluid aromatic substance. The angle-adjustable aroma diffuser of the invention facilitates replacement of the aroma device and safety use, and can be carried to any place for application.

DETAILED DESCRIPTION OF THE PREFERRED EMBODIMENT

Figure 4:
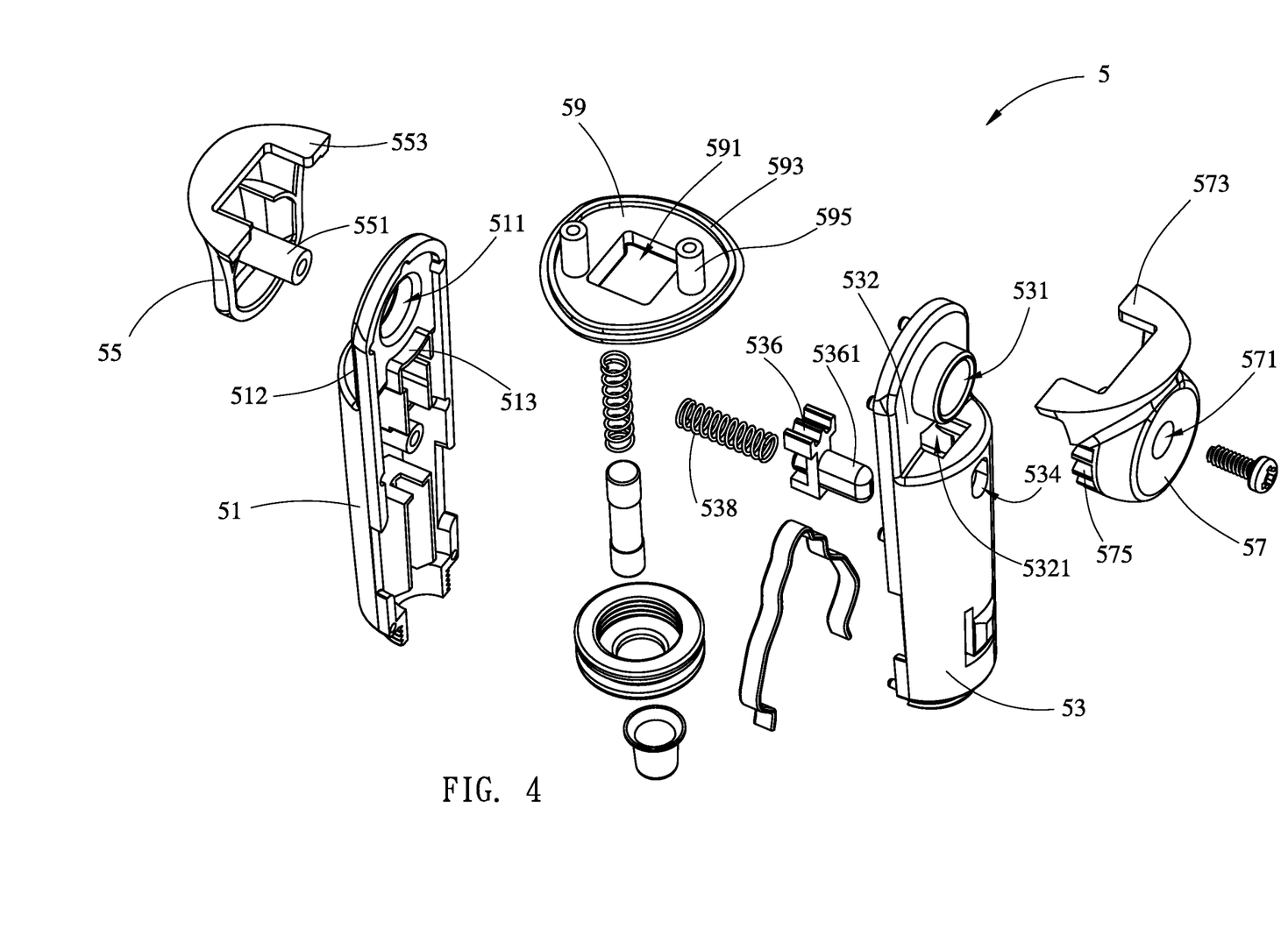
FIG. 4 is an exploded view of the electric plug of the angle-adjustable aroma diffuser in accordance with the present invention.
Figure 5A:
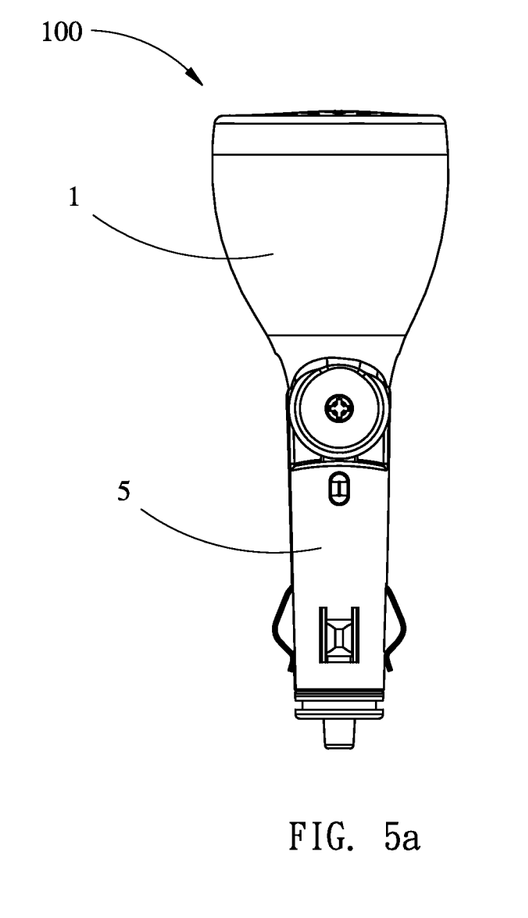
FIG. 5a & FIG. 5b are schematic drawing illustrating adjustment of the relative position between the housing and electric plug of the angle-adjustable aroma diffuser in accordance with the present invention.
Figure 5B:
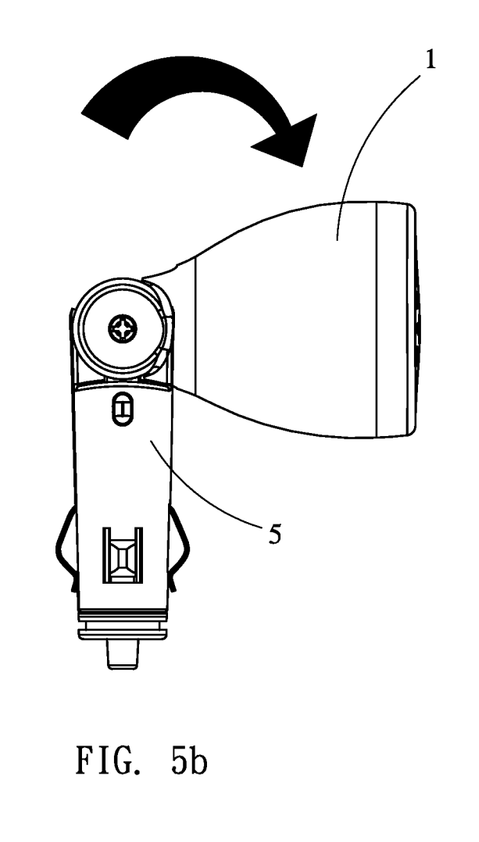

Referring to FIGS. 1-4, an angle-adjustable aroma diffuser (100) in accordance with the present invention is shown. The angle-adjustable aroma diffuser (100) comprises a housing (1), an aroma container (2), a resistor (3), and an electric plug (5). The housing (1) defines a first opening (11) at a top side thereof and a second opening (13) at a bottom side thereof. The aroma container (2) is mounted in the housing (1), having a top open side (21) facing toward the first opening (11) of the housing (1). The resistor (3) is mounted at the bottom side of the aroma container (2). The electric plug (5) is coupled to the second opening (13) of the housing (1) and electrically to the resistor (3) such that the housing (1) and the electric plug (5) are rotatable relative to each other to adjust the relative angular position. Further, the electric plug (5) is electrically connectable to a power source. As illustrated in FIG. 5, the housing (1) of the angle-adjustable aroma diffuser (100) can be biased relative to the electric plug (5) between a vertical position where the first opening (11) of the housing (1) and the top open side (21) of the aroma container (2) are facing upward, and a horizontal position where the first opening (11) of the housing (1) and the top open side (21) of the aroma container (2) are facing horizontally sideways. When the housing (1) is held in a vertical position, the user can put an aroma device (700) through the first opening (11) of the housing (1) and the top open side (21) of the aroma container (2) into the inside of the aroma container (2). When electricity is conducted from the power source to the electric plug (5) and the resistor (3), the resistor (3) creates heat that is transferred to the aroma container (2) to heat the aroma device (700) (see FIG. 6), causing the aroma device (700) to give off a pleasant smell that flows upwardly out of the angle-adjustable aroma diffuser (100). As the housing (1) and the electric plug (5) are biasable relative to each other, the user can change the relative angular position between the housing (1) and the electric plug (5) to reduce the size of the aroma container (2), saving the storage space.

The electric plug (5) of the angle-adjustable aroma diffuser (100) can be connected to a power socket in a car, house or any other place. After installation, the housing (1) can be biased relative to the electric plug (5) to the position where the top open side (21) of the aroma container (2) and the aroma device (700) in the aroma container (2) are kept facing upward, avoiding falling of the aroma device (700) out of the angle-adjustable aroma diffuser (100). Thus, the angle-adjustable aroma diffuser (100) is practical for use in a car, bicycle, aircraft, office or house.

Figure 1:
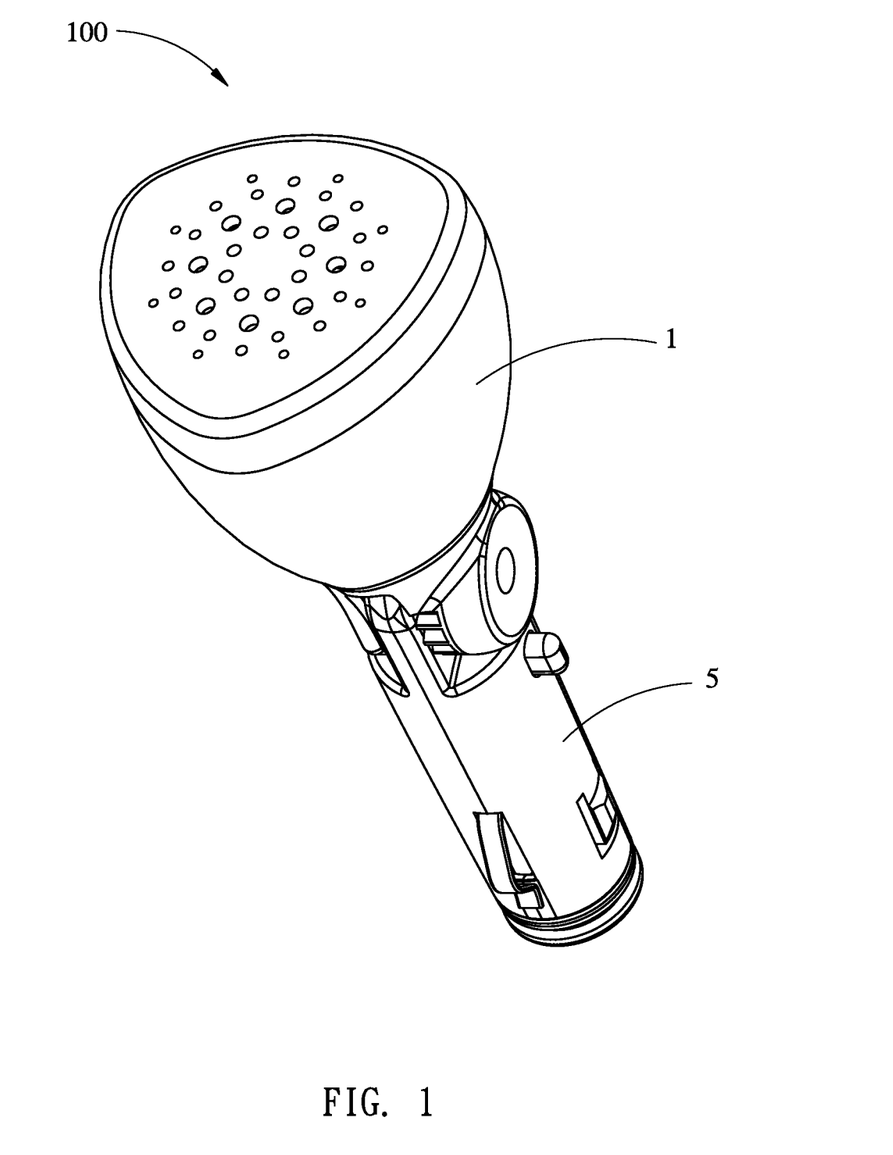
FIG. 1 is an elevational view of an angle-adjustable aroma diffuser in accordance with the present invention.
Figure 2:
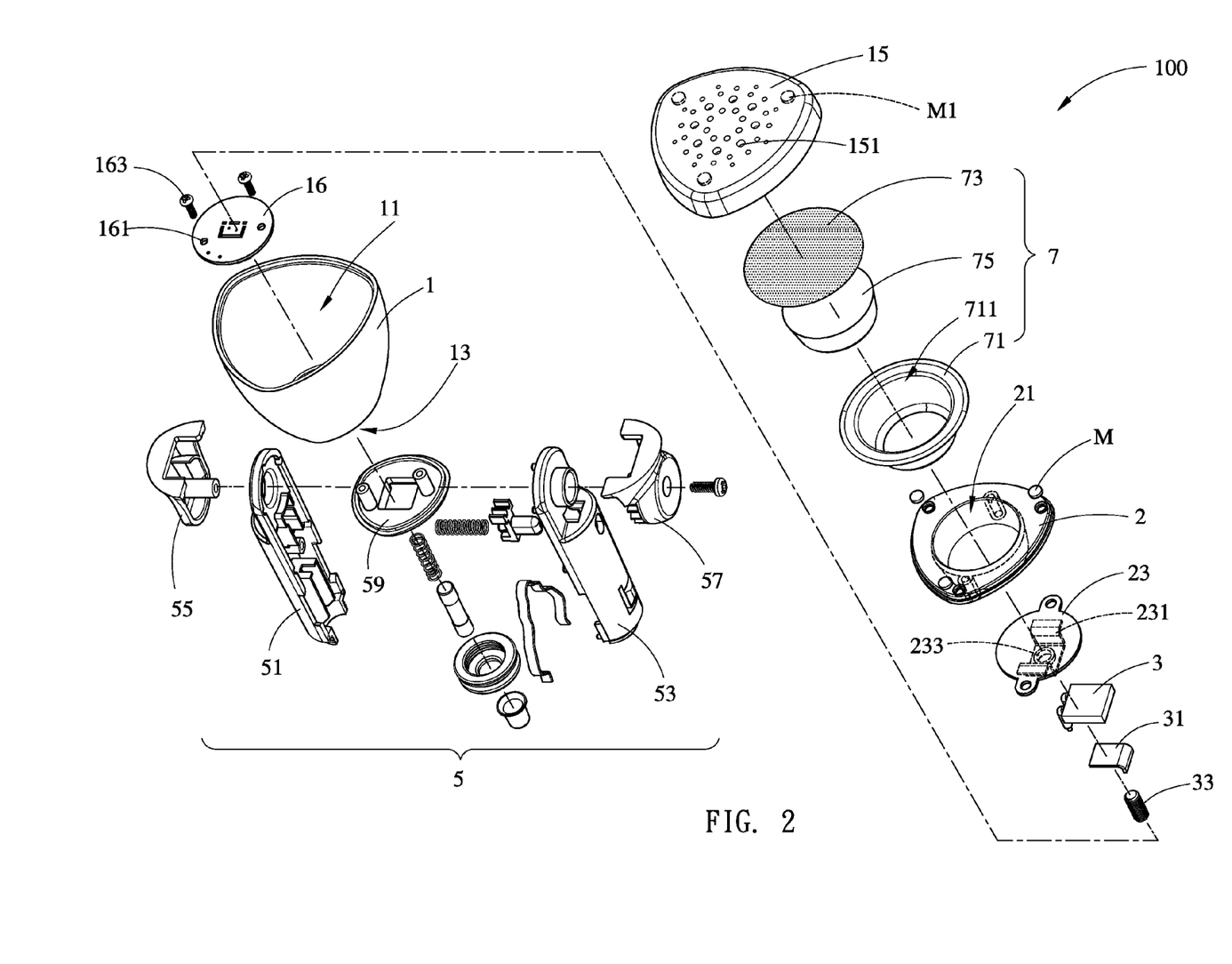
FIG. 2 is an exploded view of the angle-adjustable aroma diffuser in accordance with the present invention.
Figure 3A:
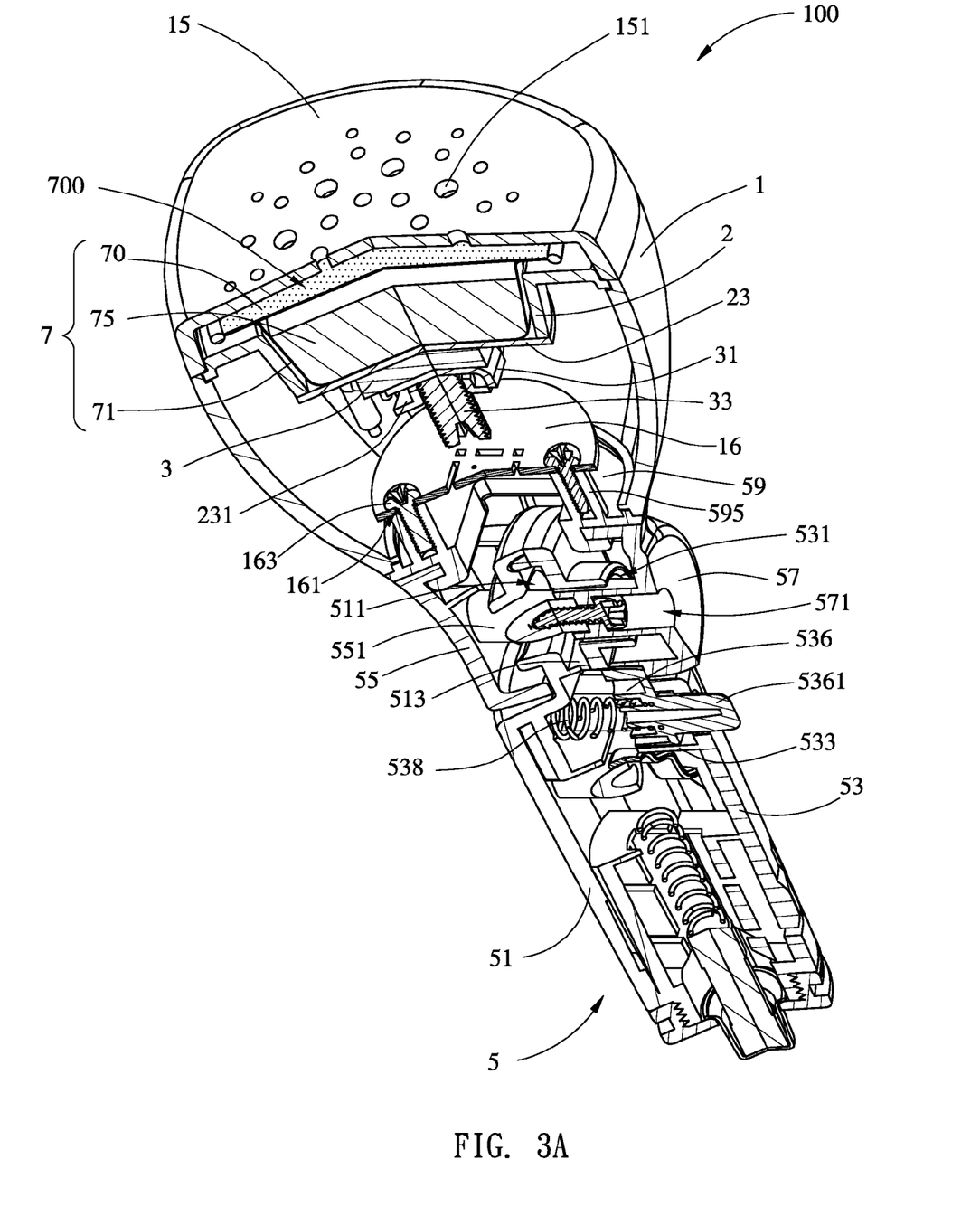
FIG. 3A is a sectional elevation of the angle-adjustable aroma diffuser in accordance with the present invention (I).
Figure 3B:
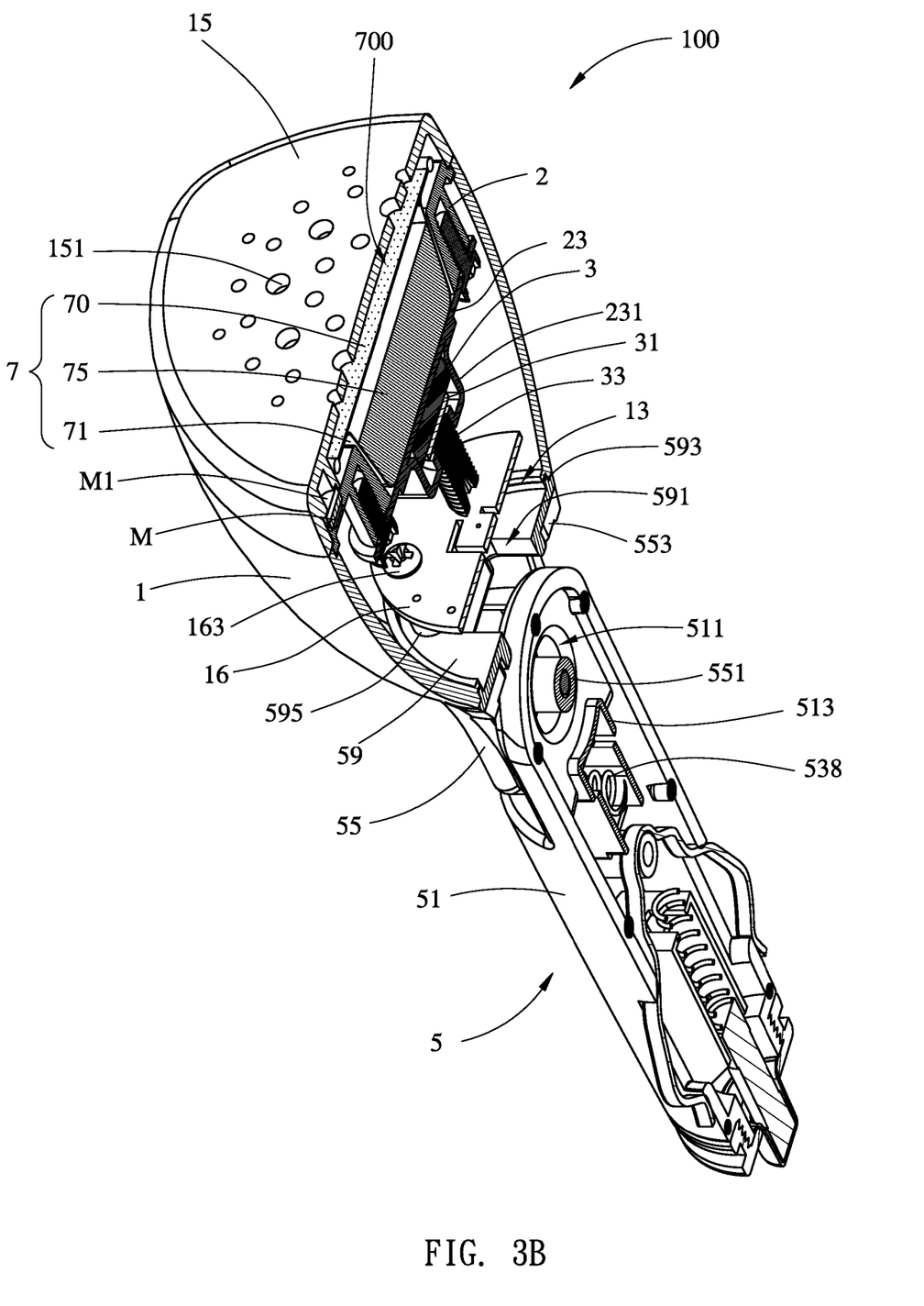
FIG. 3B is a sectional elevation of the angle-adjustable aroma diffuser in accordance with the present invention (II).

The angle-adjustable aroma diffuser (100) further comprises a bracket (231) mounted at the bottom side of the aroma container (2) to hold the resistor (3) in direct contact with the aroma container (2), a cushion pad (31) accommodated in the bracket (231) at the bottom side of the resistor (3), and a holding-down screw (33) threaded into the bracket (231) and stopped at the cushion pad (31) against the resistor (3) and the aroma container (2).

Referring to FIGS. 1-5b again, the electric plug (5) comprises a front plug shell (51), a rear plug shell (53), a front cap (55), and a rear cap (57). The front plug shell (51) comprises a first axle hole (511). The rear plug shell (53) comprises a second axle hole (531). The front cap (55) comprises an axle (551). The rear cap (57) comprises a third axle hole (571). The front plug shell (51) and the rear plug shell (53) are fastened together. The rear cap (57) is coupled to one side of the rear plug shell (53). The first axle hole (511), the second axle hole (531) and the third axle hole (571) are kept in communication with one another in a line. The front cap (55) is coupled to one side of the front plug shell (51) with the axle (551) thereof inserted through the first axle hole (511), the second axle hole (531) and the third axle hole (571). The electric plug (5) is connectable to an electric socket for power input. The housing (1) and aroma container (2) of the angle-adjustable aroma diffuser (100) can be rotated with the axle (551) of the front cap (55) and the rear cap (57) relative to the front plug shell (51) and rear plug shell (53) of the electric plug (5) between the aforesaid horizontal position and vertical position. Thus, the user can adjust the angular position of the housing (1) relative to the electric plug (5) and the attached electric socket to keep the first opening (11) of the housing (1) and the top open side (21) of the aroma container (2) facing upward. At this time, the user can put an aroma device (700) through the first opening (11) of the housing (1) and the top open side (21) of the aroma container (2) into the inside of the aroma container (2), enabling the aroma device (700) to be heated to give off a pleasant smell.

Further, the front cap (55) comprises a first top flange (553) located at the top side thereof. The rear cap (57) comprises a second top flange (573) located at the top side thereof. The electric plug (5) further comprises a connection plate (59). The connection plate (59) comprises a center opening (591) for the passing of a power cord to electrically connect the electric plug (5) to the resistor (3), and a mounting groove (593) extending around the center opening (591) for the mounting of the first top flange (553) of the front cap (55) and the second top flange (573) of the rear cap (57). The connection plate (59) is fastened to the second opening (13) of the housing (1). Thus, the front cap (55) and rear cap (57) of the electric plug (5) are connected to the housing (1) by the connection plate (59).

The angle-adjustable aroma diffuser (100) further comprises a PC board (16) (see FIG. 2) mounted inside the housing (1) and electrically coupled with the electric plug (5) and the resistor (3). The PC board (16) comprises at least one, for example, two screw holes (161). The connection plate (59) comprises at least one, for example, two internally threaded columns (595). Screws (163) are respectively inserted through the screw holes (161) and threaded into the respective internally threaded columns (595) to affix the connection plate (59) of the electric plug (5) and the PC board (16) together.

The front plug shell (51) further comprises a first horizontal top wall (512) and a first ridge (513) upwardly extended from the first horizontal top wall (512). The aforesaid first axle hole (511) is formed in the first ridge (513). The rear plug shell (53) further comprises a second horizontal top wall (532), a second ridge (533) upwardly extended from the second horizontal top wall (532) and mating the first ridge (513) of the front plug shell (51), an engagement hole (5321) located in the second horizontal top wall (532), and an operating hole (534) disposed near the engagement hole (5321). The aforesaid second axle hole (531) is formed in the second ridge (533). The electric plug (5) further comprises a movable tooth member (536), and a spring member (538). The spring member (538) can be a coil spring or spring plate having its one end stopped against the movable tooth member (536) and its other end stopped against an inner side of the front plug shell (51). The movable tooth member (536) is mounted in between the front plug shell (51) and the rear plug shell (53), comprising a front extension rod (5361) inserted through the operating hole (534) to the outside of the plug (5). The aforesaid rear cap (57) further comprises a toothed portion (575) extending around the third axle hole (571). The movable tooth member (536) is movable in and out of the engagement hole (5321) between an engaged position where the movable tooth member (536) is engaged with the toothed portion (575) of the rear cap (57) to secure the electric plug (5) and the housing (1) firmly together and a disengaged position where the movable tooth member (536) is separated from the toothed portion (575) of the rear cap (57). When wishing to change the diffusing angle of the angle-adjustable aroma diffuser (100), push the front extension rod (5361) of the movable tooth member (536) inwardly (backwardly) to disengage the movable tooth member (536) from the toothed portion (575) and to compress the spring member (538), allowing adjustment of the angular position of the housing (1) with the internal aroma container (2) relative to the electric plug (5). After adjustment, release the pressure from the front extension rod (5361), enabling the spring member (538) to push the movable tooth member (536) backwardly into engagement with the toothed portion (575), and thus the electric plug (5) and the housing (1) are locked in the adjusted condition where the top open side (21) of the aroma container (2) is kept facing upward. At this time, the aroma device (700) being heated in the aroma container (2) can release a pleasant smell through the top open side (21) of the aroma container (2) and the first opening (11) of the housing (1) into the outside open air.

Referring to FIG. 2 again, a heat-transfer plate (23) is fixedly mounted in a bottom open side of the aroma container (2) and fastened to the bracket (231). Thus, the heat-transfer plate (23) forms a bottom wall for the aroma container (2). The aforesaid resistor (3) and the cushion pad (31) are arranged together and set in between the heat-transfer plate (23) and the bracket (231). The bracket (231) comprises a screw hole (233). The aforesaid holding-down screw (33) is threaded into the screw hole (233) of the bracket (231) and stopped at the cushion pad (31) against the resistor (3) and the heat-transfer plate (23). Further, the aroma container (2) is made of a thermal insulation material. Further, the heat-transfer plate (23) is a metal plate member for transferring heat from the resistor (3) to the aroma container (2) to heat the loaded aroma device (700). Because the aroma container (2) itself is thermally insulative, heat can be directly transferred by the heat-transfer plate (23) from the resistor (3) to the aroma device (700) without causing temperature rise in the surrounding component parts.

Figure 6:
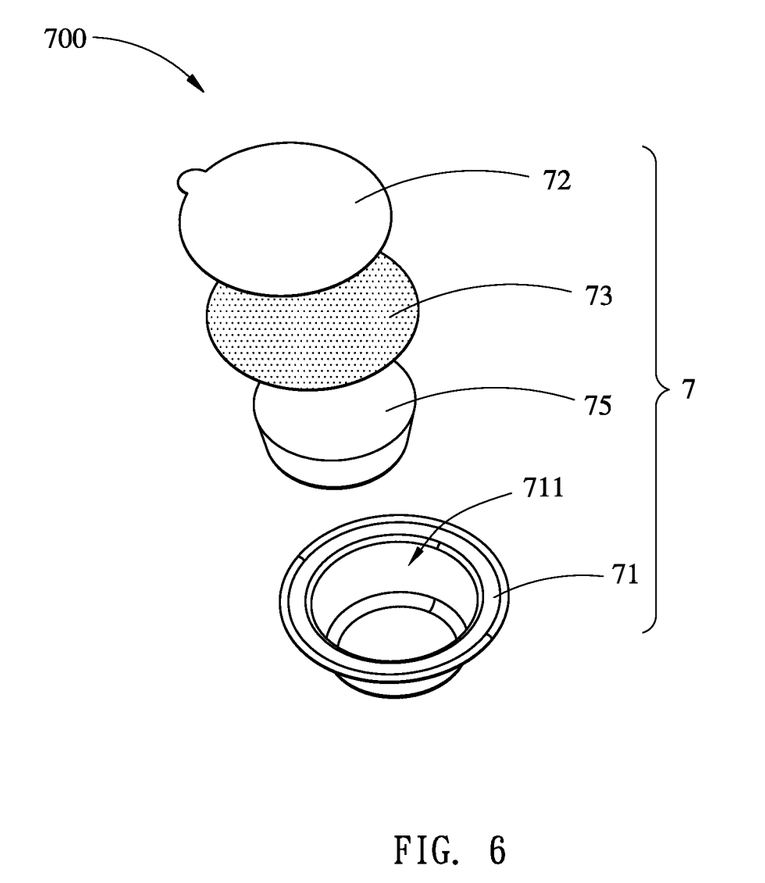
FIG. 6 is an exploded view of the aroma capsule of the angle-adjustable aroma diffuser in accordance with the present invention.

Referring to FIG. 6 and FIGS. 2, 3A and 3B again, the aroma container (2) of the angle-adjustable aroma diffuser (100) is adapted to hold an aroma device (700), enabling the aroma device (700) to be heated to create a pleasant smell. Preferably, the aroma device (700) is disposable. For example, the aroma device (700) can be an aroma capsule, aroma stone, an absorber (sponge, nonwoven fabric, cotton cloth) absorbing an essential oil or aromatic substance. After the use, the aroma device (700) can be thrown away. Thus, the angle-adjustable aroma diffuser of the invention facilitates replacement of the aroma device and safety use, and can be carried to any place for application.

According to the present preferred embodiment, the aroma device (700) is an aroma capsule (7). The aroma capsule (7) comprises a disposable capsule body (71) defining a top opening (711), and an aromatic substance (75) (for example, an aromatic wax or aroma block) put in the disposable capsule body (71). Further, the aromatic substance (75) can be a solid aromatic wax, essential oil, or perfume. In this example, the aromatic substance (75) is a solid aromatic wax. Thus, when the resistor (3) is electrically conducted, it creates heat that is then transferred by the heat-transfer plate (23) to the disposable capsule body (71) to heat the aromatic substance (75), causing the aromatic substance (75) to give off a pleasant smell.

Referring to FIGS. 2 and 6 again, the aroma capsule (7) further comprises a breathing film (73) sealed to the top opening (711) over the aromatic substance (75). The sealing film (72) is perforated for enabling the pleasant smell released by the aromatic substance (75) to float into the outside open air. Further, the breathing film (73) can be selected from the group of woven fabrics, fiber sheet materials, perforated plastic films and perforated metal foils. In the present preferred embodiment, the breathing film (73) is a perforated plastic film bonded to the disposable capsule body (71) over the top opening (711). If the angle-adjustable aroma diffuser (100) falls to the ground accidentally, the breathing film (73) can stop the melted aromatic wax from flowing out of the disposable capsule body (71) to contaminate surrounding objects or to cause danger.

Referring to FIG. 6 again, the aroma capsule (7) further comprises a sealing film (72) bonded to the disposable capsule body (71) to seal the aromatic substance (75) in the disposable capsule body (71) and to protect the aromatic substance (75) against contamination during delivery. Before putting the aroma capsule (7) in the aroma container (2) for application, the sealing film (72) must be removed from the disposable capsule body (71). Further, the disposable capsule body (71) can be selected from the group of metals, hard plastics, fibers (corn fiber, glass fiber, carbon fiber) and compound materials, and made in the shape of a bowl. Preferably, the disposable capsule body (71) is made of aluminum foil for the advantages of light weight and excellent thermal conductivity. Thus, the disposable capsule body (71) can transfer heat from the heat-transfer plate (23) to the aromatic substance (75) rapidly, causing the aromatic substance (75) to give off a pleasant smell. When compared to conventional ceramic bowls or containers that are commonly used in conventional aroma diffusers for hold an essential oil or aromatic wax, the disposable capsule body (71) does not break easily.

Further, because the aromatic substance (75) is contained in the disposable capsule body (71), the user does not touch the aromatic substance (75) when removing the sealing film (72) from the disposable capsule body (71). Further, after the use of the aroma capsule (7), the user can thrown the disposable capsule body (71) away without washing it, and then put a new piece of aroma capsule (7) in the aroma container (2) for giving off a pleasant smell. Further, aroma capsules (7) containing different aromatic substances (75) for giving off different pleasant smells can be selectively used and put in the aromatic container (2).

Figure 7:
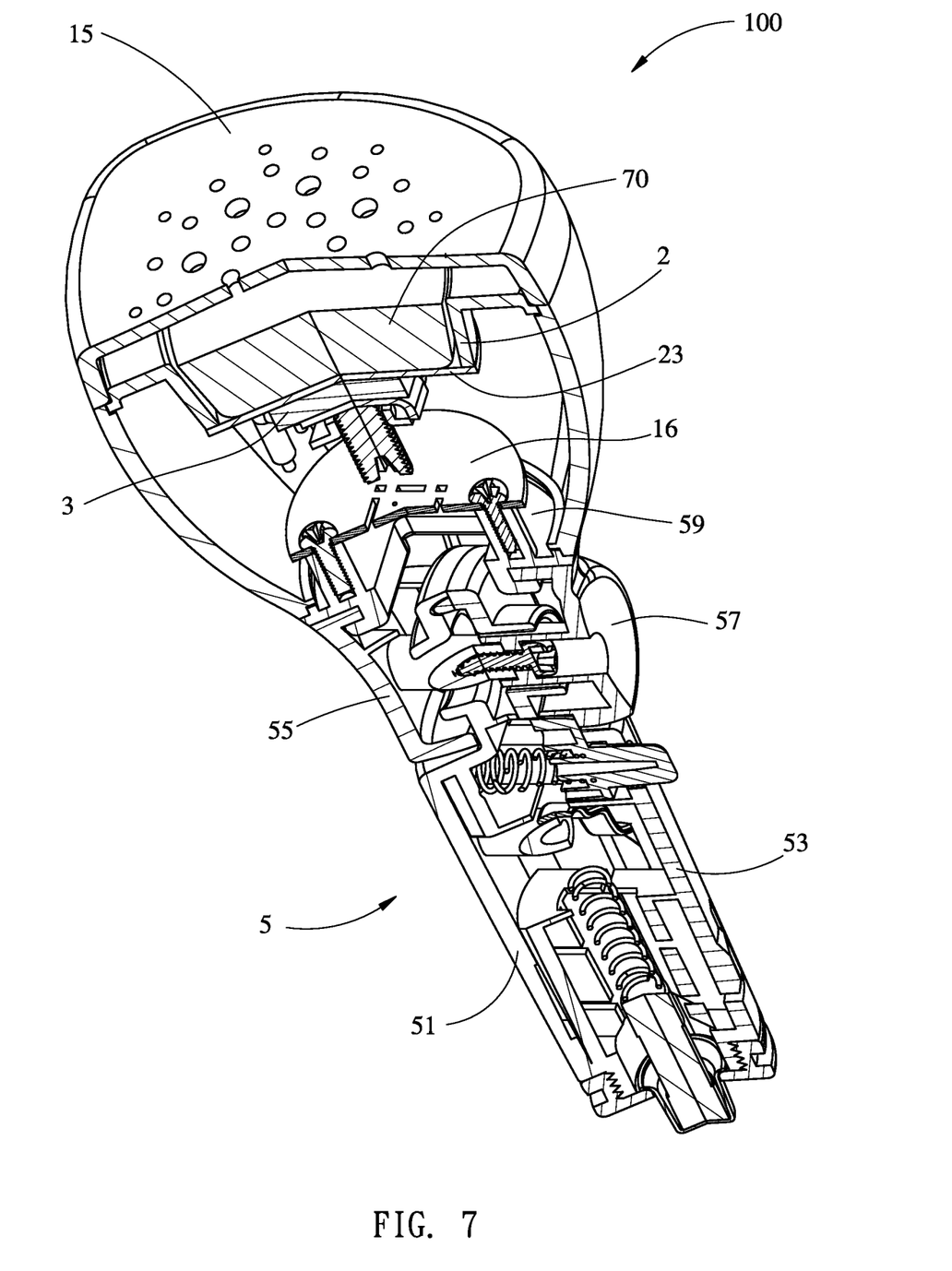
FIG. 7 is a sectional elevational view of an alternate form of the present invention, illustrating an aroma stone accommodated in the aroma container.

Referring to FIG. 7, a porous aroma stone (70) can be used and put in the aromatic container (2) to substitute for the aforesaid aroma capsule (7) or aroma device (700). The porous aroma stone (70) can be a piece of porous ceramic block, plaster block, fiber block, colloidal plate, soap block, paper block or wooden block, having filled therein an aromatic substance, such as essential oil, artificial essence, flower essence or perfume.

Preferably, the porous aroma stone (70) is a porous ceramic member having filled therein an essential oil. When the porous aroma stone (70) is heated by the heat created by the resistor (3), releasing essential oil vapors into the air. Further, a instead of the aforesaid porous aroma stone, a sponge can be used to absorb an essential oil for application.

Because the porous aroma stone (70) holds the essential oil by the siphon effect, replacing the porous aroma stone (70) does not cause contaminate the user's hand. When the porous aroma stone (70) is used out, the user can remove the used porous aroma stone (7) and put a new porous aroma stone (7) in the aroma container (2) conveniently and rapidly. Even if the aroma diffuser falls to the ground accidentally, the contained essential oil will not flow out of the aroma container (2) to contaminate the resistor (3).

Further, the aforesaid electric plug (5) can be configured for car use, i.e., it can be electrically connected to an electric socket in a motor vehicle.

Referring to FIGS. 1-4 again, the angle-adjustable aroma diffuser (100) further comprises a cover (15) having a plurality of air vents (151). The cover (15) is detachably fastened to the top open side (21) of the aroma container (2). Further, magnets (M;M1) are respectively and reversely mounted at the top side of the aroma container (2) and the bottom side of the cover (15) for detachably securing the cover (15) and the aroma container (2) by magnetic attraction.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An angle-adjustable aroma diffuser, comprises:
    a housing defining a first opening and second opening opposite to said first opening;
    an aroma container mounted in said housing for holding an aroma substance, said aroma container defining a top open side facing toward said first opening of said housing;
    a resistor provided at a bottom side of said aroma container and adapted for creating heat to heat an aroma substance being put in said aroma container;
    an electric plug pivotally coupled to said second opening of said housing and electrically connected with said resistor;
    said electric plug comprises a front plug shell, a rear plug shell, a front cap and a rear cap;
    said front plug shell comprises a first axle hole;
    said rear plug shell comprises a second axle hole in axial alignment with said first axle hole;
    said front cap comprises an axle;
    said rear cap comprises a third axle hole in axial alignment with said first axle hole and said second axle hole;
    said front plug shell and said rear plug shell being fastened together and fixedly connected to said housing;
    said rear cap being capped on one lateral side of said rear plug shell; and
    said front cap being capped on one lateral side of said front plug shell to insert said axle through said first axle hole and said second axle hole and fastened to said third axle hole so that said front cap and said rear cap are biasable with said housing relative to said front plug shell and said rear plug shell within a predetermined angle.

2. The angle-adjustable aroma diffuser as claimed in claim 1, wherein said electric plug further comprises a connection plate fastened to said second opening of said housing, said connection plate defining a center opening and a mounting groove around said center opening; said front cap further comprises a first top flange located at a top side thereof and fastened to said mounting groove of said connection plate; said rear cap comprises a second top flange located at a top side thereof and fastened to said mounting groove of said connection plate and abutted against said first top flange of said front cap.

3. The angle-adjustable aroma diffuser as claimed in claim 2, further comprising a PC board mounted in said housing and electrically connected with said electric plug and said resistor, said PC board comprising a screw hole), wherein said connection plate comprises an internally threaded column connected to said screw hole of said PC board by a screw.

4. The angle-adjustable aroma diffuser as claimed in claim 1, wherein said front plug shell further comprises a first horizontal top wall, a first ridge upwardly extended from said first horizontal top wall; said first axle hole is formed in said first ridge; said rear plug shell comprises a second horizontal top wall, an engagement hole located in said second horizontal top wall, a second ridge upwardly extended from second horizontal top wall; said second axle hole is formed in said second ridge; said rear plug shell further comprises an operating hole disposed near said engagement hole; said rear cap further comprises a toothed portion extending around said third axle hole; said electric plug further comprises a movable tooth member and a spring member, said spring member having one end thereof stopped at said movable tooth member and an opposite end thereof stopped at an inner side of said front plug shell, said movable tooth member comprising a front extension rod inserted through said operating hole toward the outside of said electric plug, said front extension rod being operable by a user to move said movable tooth member in and out of said engagement hole between an engaged position where said movable tooth member is engaged with said toothed portion to lock said housing to said electric plug and a disengaged position where said movable tooth member is disengaged from said toothed portion for allowing said housing to be biased relative to said electric plug.

5. The angle-adjustable aroma diffuser as claimed in claim 2, wherein said front plug shell further comprises a first horizontal top wall, a first ridge upwardly extended from said first horizontal top wall; said first axle hole is formed in said first ridge; said rear plug shell comprises a second horizontal top wall, an engagement hole located in said second horizontal top wall, a second ridge upwardly extended from second horizontal top wall; said second axle hole is formed in said second ridge; said rear plug shell further comprises an operating hole disposed near said engagement hole; said rear cap further comprises a toothed portion extending around said third axle hole; said electric plug further comprises a movable tooth member and a spring member, said spring member having one end thereof stopped at said movable tooth member and an opposite end thereof stopped at an inner side of said front plug shell, said movable tooth member comprising a front extension rod inserted through said operating hole toward the outside of said electric plug, said front extension rod being operable by a user to move said movable tooth member in and out of said engagement hole between an engaged position where said movable tooth member is engaged with said toothed portion to lock said housing to said electric plug and a disengaged position where said movable tooth member is disengaged from said toothed portion for allowing said housing to be biased relative to said electric plug.

6. The angle-adjustable aroma diffuser as claimed in claim 3, wherein said front plug shell further comprises a first horizontal top wall, a first ridge upwardly extended from said first horizontal top wall; said first axle hole is formed in said first ridge; said rear plug shell comprises a second horizontal top wall, an engagement hole located in said second horizontal top wall, a second ridge upwardly extended from second horizontal top wall; said second axle hole is formed in said second ridge; said rear plug shell further comprises an operating hole disposed near said engagement hole;
    said rear cap further comprises a toothed portion extending around said third axle hole;
    said electric plug further comprises a movable tooth member and a spring member, said spring member having one end thereof stopped at said movable tooth member and an opposite end thereof stopped at an inner side of said front plug shell, said movable tooth member comprising a front extension rod inserted through said operating hole toward the outside of said electric plug, said front extension rod being operable by a user to move said movable tooth member in and out of said engagement hole between an engaged position where said movable tooth member is engaged with said toothed portion to lock said housing to said electric plug and a disengaged position where said movable tooth member is disengaged from said toothed portion for allowing said housing to be biased relative to said electric plug.

7. The angle-adjustable aroma diffuser as claimed in claim 1, further comprising an aroma device mounted in said aroma container and heatable by said resistor to release vapors.

8. The angle-adjustable aroma diffuser as claimed in claim 1, wherein said disposable aroma device is an aroma capsule, said aroma capsule comprising a disposable capsule body defining a top opening, an aromatic substance put in said disposable capsule body, and a sealing film bonded to said disposable capsule body to seal said aromatic substance in said disposable capsule body.

9. The angle-adjustable aroma diffuser as claimed in claim 8, wherein said aromatic substance is an aromatic wax.

10. The angle-adjustable aroma diffuser as claimed in claim 8, wherein said aroma capsule further comprises a breathing film sealed to the top opening of said disposable capsule body over said aromatic substance and covered by said sealing film.

11. The angle-adjustable aroma diffuser as claimed in claim 10, wherein said breathing film is selected from the group of woven fabrics, fiber sheet materials, perforated plastic films and perforated metal foils.

12. The angle-adjustable aroma diffuser as claimed in claim 8, wherein said disposable capsule body is selected from the group of metal, hard plastics, fibers and compound materials, and made in the shape of a bowl.

13. The angle-adjustable aroma diffuser as claimed in claim 1, further comprising a porous aroma stone accommodated in said aroma container, said porous aroma stone having filled therein an aromatic substance.

14. The angle-adjustable aroma diffuser as claimed in claim 13, wherein said aroma stone is selected from the group of porous ceramic block, plaster block, fiber block, colloidal plate, soap block, paper block and wooden block.

15. The angle-adjustable aroma diffuser as claimed in claim 6, further comprising an aroma device accommodated in said aroma container and heatable to release vapors.

16. The angle-adjustable aroma diffuser as claimed in claim 6, further comprising an aroma capsule accommodated in said aroma container, said aroma capsule comprising a disposable capsule body defining a top opening, an aromatic substance accommodated in said disposable capsule body.

17. The angle-adjustable aroma diffuser as claimed in claim 16, wherein said aroma capsule further comprises a breathing film bonded to said disposable capsule body over said top opening.

18. The angle-adjustable aroma diffuser as claimed in claim 6, further comprising a porous aroma stone accommodated in said aroma container, said porous aroma stone having filled therein an aroma substance.

19. The angle-adjustable aroma diffuser as claimed in claim 1, wherein said electric plug is configured for connection to an electric socket in a motor vehicle for receiving a vehicle battery power supply.

20. The angle-adjustable aroma diffuser as claimed in claim 1, wherein said aroma container comprises a bottom wall formed of a heat-transfer plate, a bracket fastened to said heat-transfer plate to hold said resistor is direct contact with said heat-transfer plate, said bracket defining therein a screw hole, a cushion pad set in between said resistor and said bracket, and a holding-down screw threaded into said screw hole and stopped at said cushion pad against said resistor and said heat-transfer plate.

* * * * *